(12) United States Patent
Tzeng (10) Patent No.: US 9,055,781 B2
(45) Date of Patent: Jun. 16, 2015

(54) BODY BALANCE DEVICE

(75) Inventor: Tzann-Yuh Tzeng, Taipei (TW)

(73) Assignee: Varithotics Co., Ltd., Taipei (TW)

( * ) Notice: Subject to any disclaimer, the term of this patent is extended or adjusted under 35 U.S.C. 154(b) by 283 days.

(21) Appl. No.: 13/526,556

(22) Filed: Jun. 19, 2012

(65) Prior Publication Data
US 2012/0255199 A1    Oct. 11, 2012

Related U.S. Application Data (63) Continuation-in-part of application No. 12/575,809, filed on Oct. 8, 2009, now abandoned.

(51) Int. Cl.
  *A43B 7/14*   (2006.01)
  *A43B 17/00*  (2006.01)
  *A61F 5/14*   (2006.01)

(52) U.S. Cl.
  CPC .............. *A43B 17/00* (2013.01); *A43B 7/1415* (2013.01); *A43B 7/1405* (2013.01); *A43B 7/1425* (2013.01); *A43B 7/143* (2013.01); *A43B 7/1435* (2013.01); *A43B 7/144* (2013.01); *A43B 7/148* (2013.01); *A61F 5/14* (2013.01)

(58) Field of Classification Search
  CPC ... A43B 7/1405; A43B 7/1415; A43B 7/1485
  USPC ........ 36/88, 43, 140, 145, 166, 174, 180, 181
  See application file for complete search history.

(56) References Cited

U.S. PATENT DOCUMENTS

| | | | | |
|---|---|---|---|---|
| 975,576 | A * | 11/1910 | Sexton | 36/43 |
| 1,597,131 | A * | 8/1926 | Wentworth | 36/145 |
| 1,741,419 | A * | 12/1929 | Jones | 36/145 |
| 1,960,418 | A * | 5/1934 | Johannes | 36/178 |
| 2,037,970 | A * | 4/1936 | Everston | 36/19 R |
| 3,086,532 | A * | 4/1963 | Mistarz | 36/145 |
| 4,557,060 | A * | 12/1985 | Kawashima | 36/44 |
| 4,697,361 | A * | 10/1987 | Ganter et al. | 36/28 |
| 4,793,078 | A * | 12/1988 | Andrews | 36/43 |
| 5,438,768 | A * | 8/1995 | Bauerfeind | 36/44 |
| 5,695,850 | A * | 12/1997 | Crow | 428/139 |
| 5,746,011 | A * | 5/1998 | Hedstrom | 36/44 |
| 6,120,880 | A * | 9/2000 | Crow | 428/167 |
| 6,176,025 | B1 * | 1/2001 | Patterson et al. | 36/28 |
| 6,453,578 | B1 * | 9/2002 | Yung et al. | 36/43 |
| 6,589,630 | B1 * | 7/2003 | Crow | 428/167 |
| 6,684,532 | B2 * | 2/2004 | Greene et al. | 36/28 |
| 7,107,705 | B2 * | 9/2006 | Dalton et al. | 36/44 |
| 7,614,163 | B2 * | 11/2009 | Fujii | 36/43 |
| 7,832,119 | B2 * | 11/2010 | Gilmore | 36/44 |

(Continued)

*Primary Examiner* — Marie Bays (74) *Attorney, Agent, or Firm* — Juan Carlos A. Marquez; Bacon & Thomas PLLC (57) ABSTRACT

The present invention relates to a body balance device, which includes a main body made of a cushioning material. The main body includes a first metatarsal bone section, a fourth metatarsal bone section, and a foot heel section. The main body forms a primary adjustment structure located between the first metatarsal bone section and the fourth metatarsal bone section and a secondary adjustment structure located between the fourth metatarsal bone section and the foot heel section and corresponding to outside of the main body. Both adjustment structures are formed with a structure of through hole or cavity in which a soft material is selectively embedded to allow the human body to reach a balanced condition when standing or walking so as to improve the discomfort of bones and muscles caused by long standing or walking.

17 Claims, 13 Drawing Sheets

(56) References Cited

U.S. PATENT DOCUMENTS

| | | | |
|---|---|---|---|
| 2001/0039746 A1* | 11/2001 | Seiter | 36/44 |
| 2002/0007569 A1* | 1/2002 | Crane et al. | 36/44 |
| 2002/0092203 A1* | 7/2002 | Hardt | 36/43 |
| 2004/0118017 A1* | 6/2004 | Dalton et al. | 36/44 |
| 2005/0166425 A1* | 8/2005 | Seiter | 36/44 |
| 2006/0005428 A1* | 1/2006 | Lebo | 36/43 |
| 2007/0033834 A1* | 2/2007 | Cheskin et al. | 36/44 |
| 2012/0272545 A1* | 11/2012 | Chenut | 36/43 |

\* cited by examiner

BODY BALANCE DEVICE

CROSS-REFERENCE TO RELATED APPLICATION

This application is a continuation-in-part of the co-pending patent application Ser. No. 12/575,809 filed Oct. 2, 2009, owned by the same applicant.

TECHNICAL FIELD OF THE INVENTION

The present invention generally relates to a device that adjusts the gravity center of human body for helping long standing or walking, and in particular to a body balance device that is used by being placed inside a shoe for padding under foot sole in the same way as a shoe pad or a midsole.

DESCRIPTION OF THE PRIOR ART

The prosperous progress of economics brings more and more modern disease for the modern people. One of the commonly known and suffered modern diseases is chronic pain. One of the primary causes for the chronic pain is that bones and muscles lose balance. In the evolution history of human beings, the human beings evolved from crawling to walking in an upstanding condition. To maintain balance for standing and walking in an upright posture, human body generates an effect of compensation and such a compensation effect causes various incorrect movements and postures, which result in various sores and aches of the chronic pains. Consequently, medical experts and scientists of the related field are making their best to achieve a solution that allows joint muscles of human body to maintain at a neutral balanced position in order to eliminate sores and aches and the chronic pains caused by incorrect movements and postures.

Figure 13:
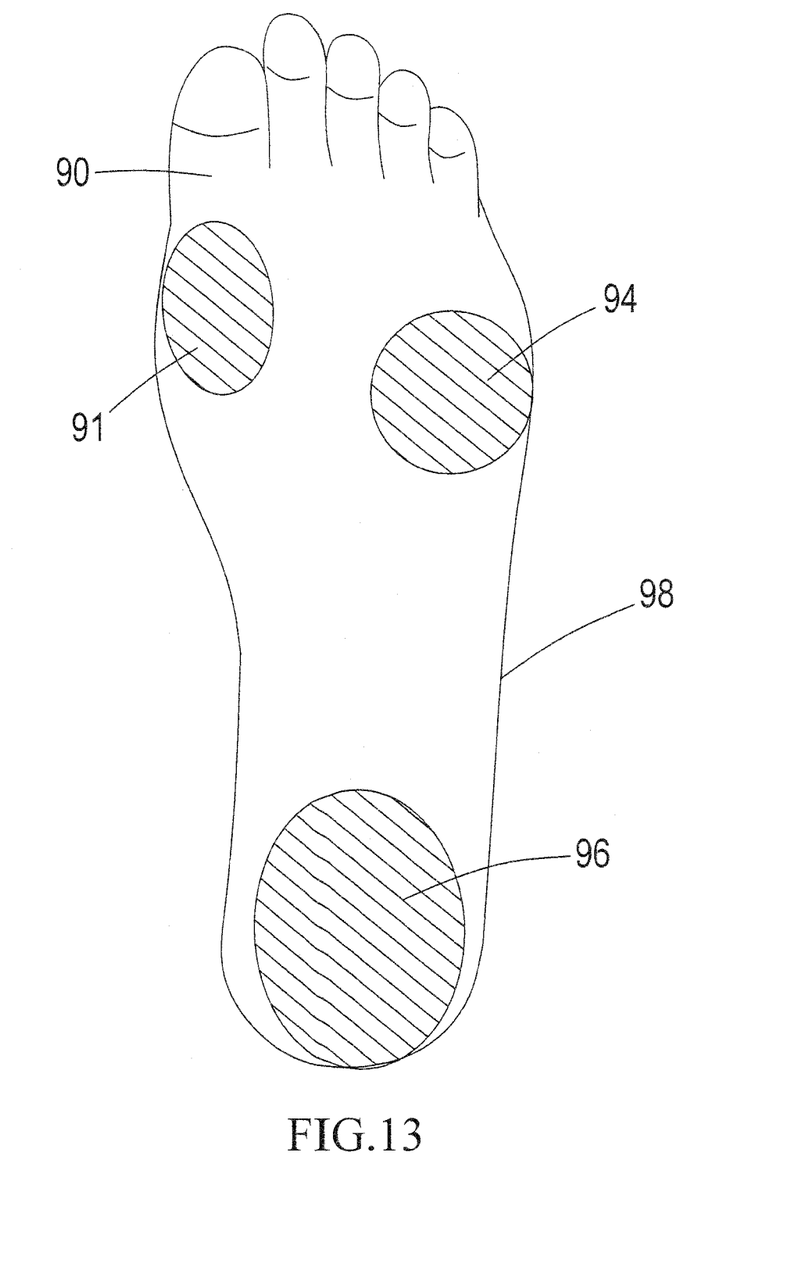
FIG. 13 is a schematic view showing a human sole.

Referring to FIG. 13, when people stand or walk, the perfect condition is that a support of three points of the site (91) of a human sole (90) which the first metatarsal bone of the sole corresponds to, site (94) of the sole which the fourth metatarsal bone corresponds to, and the heel site (96) can be formed so that the bone and muscle systems can be naturally maintained at a neutral balanced position in standing or walking.

However, a first specific portion of the sole between the first metatarsal bone site (91) and the fourth metatarsal bone site (94) will protrude more downward then the first metatarsal bone site (91) and the fourth metatarsal bone site (94) and will bear a greater force acting thereon, whereby the sole feel uncomfortable for the first specific portion when walking. This may lead eccentric shift of body weight inward or outward the sole during standing or walking and instability results. Such an unstable condition of force between inside portion and outside portion of the sole will cause discomfort and will make the whole body weight shifted toward the heel. Besides the discomfort mentioned above, this also makes sole (90) sway when walking, leading to negative influence on bones and muscles.

To improve such a problem, reduction of the force acting on the previously mentioned first specific portion must be exercised and the force so born must be spread to the first metatarsal bone site (91) and the fourth metatarsal bone site (94) to thereby form a three-point support together with the heel site (96).

On the other hand, a second specific portion of the outer side (98) of the sole, which corresponds to the outside arch between the fourth metatarsal bone site (94) and the heel site (96), might lead to splaying out of foot in standing or walking due to increased height of shoe heel and increased contact force of the sole. To improve such a problem, the force acting on the second specific portion that corresponds to the outside arch must be reduced.

Apparently, it is desired in the market to have a body balance device to reduce the forces acting both the first and second specific portion of sole. Yet, no such a device is currently available in the market to suit such a need. It is thus a challenge to be handled as soon as possible to suit such a need.

SUMMARY OF THE INVENTION

In view of the issue that the first and second specific portions of a foot sole are subjected to excessive forces, the present invention aims to provide a body balance device that reduces the force acting on the first specific portion and also reduces the force acting on the second specific portion. As such, the body balance device can be used as a foot article to allow the site of sole to which the first metatarsal bone site corresponds, the site of sole to which the fourth metatarsal bone site corresponds, and the heel site to form a three-point support, which allows the bone and muscle systems to naturally take a neutral balanced position when standing or walking to exhibit the perfect condition that allows the body structure to easily self-adjust the gravity center of the body and thus changing body posture to maintain the balance. With the present invention that helps keeping the body and muscle systems at an ideal balanced condition, damage caused by unbalance of bones and muscles can be minimized, the trouble of sores and aches and chronic pains of body can be improved, and people may feel totally comfortable and are not hurt.

To achieve the above object, the technical solution adopted in the present invention is a body balance device, which comprises:

a main body, which is positionable under a foot sole and is made of a cushioning material and comprises a top surface, a bottom surface, a first metatarsal bone section corresponding to a first metatarsal bone site of the human foot sole, a fourth metatarsal bone section corresponding to a fourth metatarsal bone site of the human foot sole, and a foot heel section corresponding to human foot heel; and at least one primary adjustment structure, which is disposed on the main body and is located between the first metatarsal bone section and the fourth metatarsal bone section, having a rectangular shape to effectively reduce a contact force incurring in the rectangular area between the first metatarsal bone section and the fourth metatarsal bone section, wherein a circular area that is excessively large may affect the contact force between the first metatarsal bone section and the fourth metatarsal bone section, the rectangular area being provided with a structure selected from a through hole structure, a soft material embedded structure, a top recessed cavity structure, a bottom recessed cavity structure, a top embedding soft material structure, a bottom embedding soft material structure, a reduced thickness thin plate structure, a top and bottom embedding soft material structure, a hollow structure, and an internally-filling soft material structure, wherein the soft material is softer than the cushioning material of the main body.

Due to the hollow or soft structure provided in the primary adjustment structure, the force that the previously discussed first specific portion of foot sole bears can be effectively reduced by distributing the force to the first metatarsal bone site and the fourth metatarsal bone site of the foot sole, and this can be applied in combination with a secondary adjustment structure. The secondary adjustment structure can be located at an outside arch between the fourth metatarsal bone section and the foot heel section. The secondary adjustment structure can be of a structure that is formed as a through hole structure, a soft material embedded structure, a top recessed cavity structure, a bottom recessed cavity structure, a top embedding soft material structure, a bottom embedding soft material structure, a reduced thickness thin plate structure, a top and bottom embedding soft material structure, a hollow structure, or an internally-filling soft material structure. As such, during standing or walking, for a second specific portion between the fourth metatarsal bone site and the heel site of the outer side of the foot sole and corresponding to an outside arch, the contact force incurring in the second specific portion can be reduced. When the contact force of the secondary adjustment structure is gradually reduced, the force acting on the outer side of the sole is reduced and the first metatarsal bone section and the fourth metatarsal bone second of sole are then allowed to actually bear the contact force. Under this condition and in combination with the arrangement of the primary adjustment structure, the heel and the sole naturally form a three-point support that allows the bone and muscle system of human body to assume an ideal balanced condition thereby eliminating or alleviating the troubles sores and aches and chronic pains. Further, the present invention can be used in combination with unsymmetrical arrangement of vamp and shoe heel height of golden ratio to allow the bone and muscle systems to naturally assume a neutral balanced position during standing or walking.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 2:
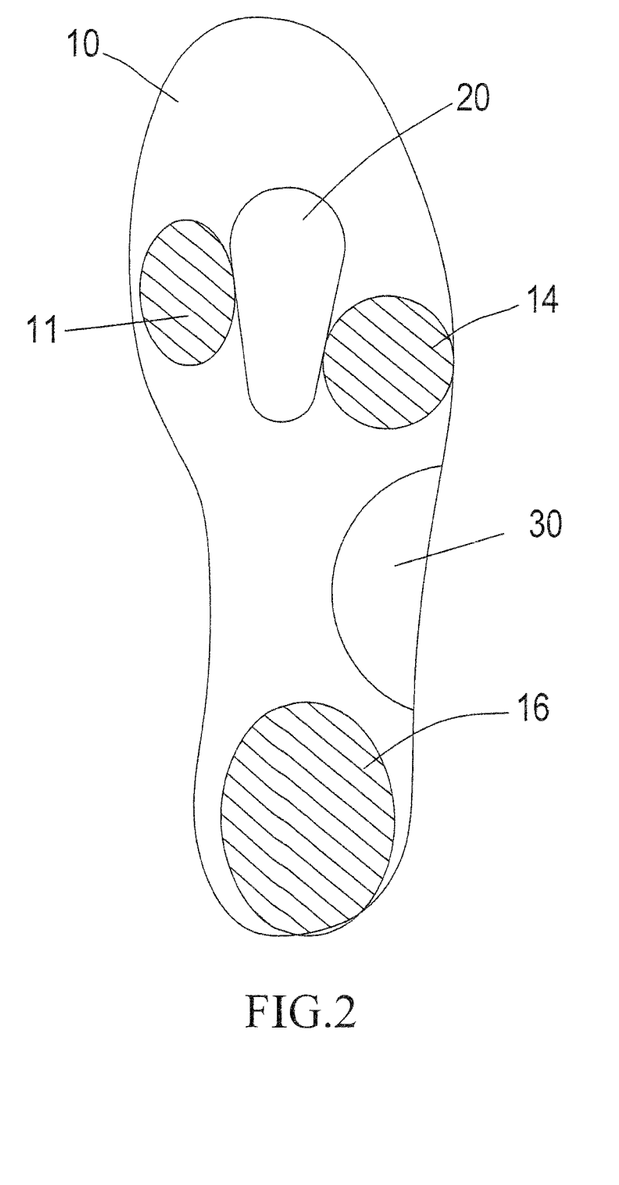
FIG. 2 is a plan view showing a preferred embodiment according to the present invention.
Figure 3:
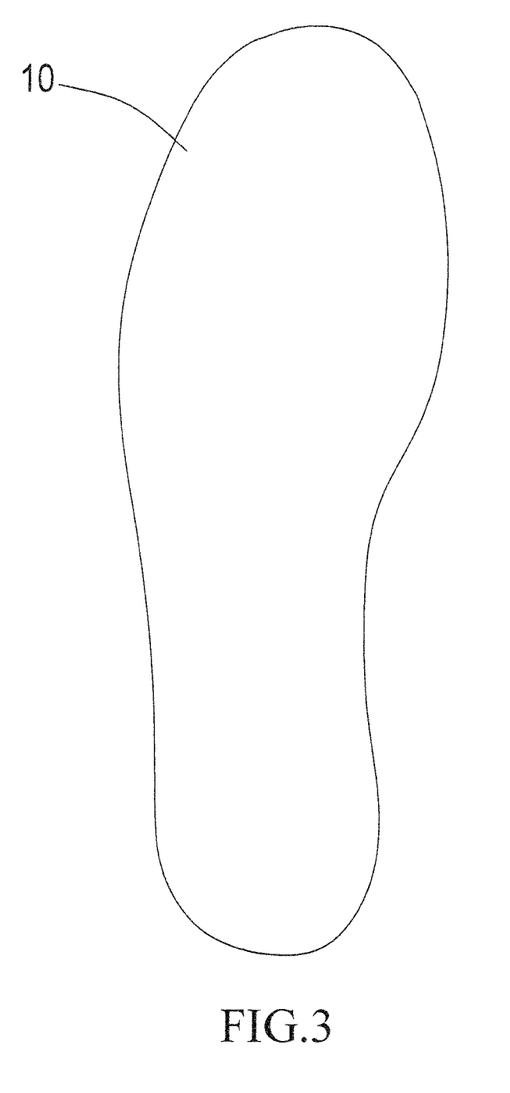
FIG. 3 is a bottom view of the preferred embodiment of the present invention.

Referring to FIGS. 2 and 3, a preferred embodiment of the present invention is a body balance device, which comprises a main body (10), a primary adjustment structure (20) disposed on the main body (10), and a secondary adjustment structure (30).

The main body (10) is to be placed under the foot sole and is generally made of a cushioning material and comprises a top surface, a bottom surface, a first metatarsal bone section (11) corresponding to a first metatarsal bone site of the human foot sole, a fourth metatarsal bone section (14) corresponding to a fourth metatarsal bone site of the human foot sole, and a foot heel section (16) corresponding to human foot heel. In the preferred embodiment, the main body (10) is made in the form of shoe pad. In other types of the preferred embodiment, the main body (10) is made in the form of a midsole. When the main body (10) is in the form of a shoe midsole, it can be disposed on an outsole of a shoe product. When the main body (10) is in the form of a shoe pad, it can be disposed on an inner bottom of a shoe according to the desire of a user in order to have the main body (10) placed under the foot sole.

Figure 1:
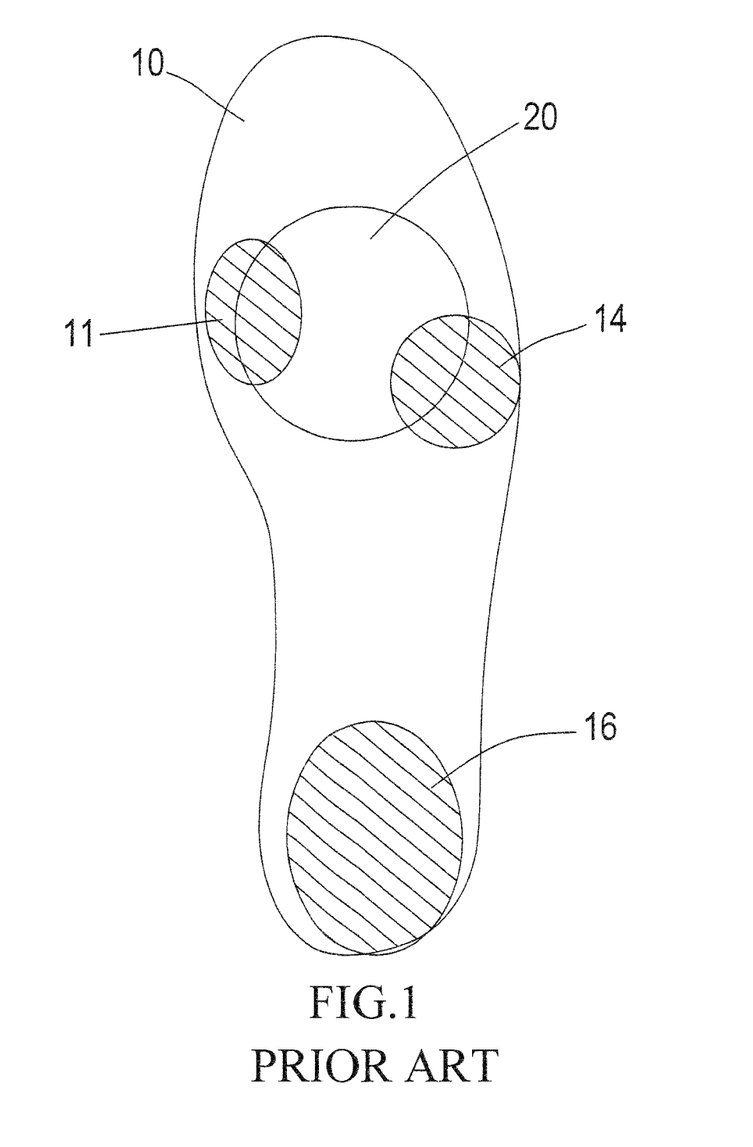
FIG. 1 is a plan view showing a known example.

The primary adjustment structure (20) is located between the first metatarsal bone section (11) and the fourth metatarsal bone section (14) and shows a rectangular shape and forms a top recessed cavity structure and extends in a direction toward the foot heel section (16) to reach a position corresponding to an upper edge of human foot arch for effectively reducing the contact force incurring in the rectangular area between the first metatarsal bone section (11) and the fourth metatarsal bone section (14). Referring to FIG. 1, if this site is made circular, then it may influence the contact force of the first metatarsal bone section (11) and the fourth metatarsal bone section (14).

The secondary adjustment structure (30) is located between the fourth metatarsal bone section (14) and the foot heel section (16). The secondary adjustment structure (30) forms a concave curve on the top surface of the main body (10) and shows a top recessed cavity structure. As such, when standing or walking, for the second specific portion of the outer side of foot sole that is located between the fourth metatarsal bone site and the foot heel site to correspond to the outside arch, it is possible to reduce the force born by the second specific portion thereby improving the potential splaying-out condition in standing or walking.

Figure 4:
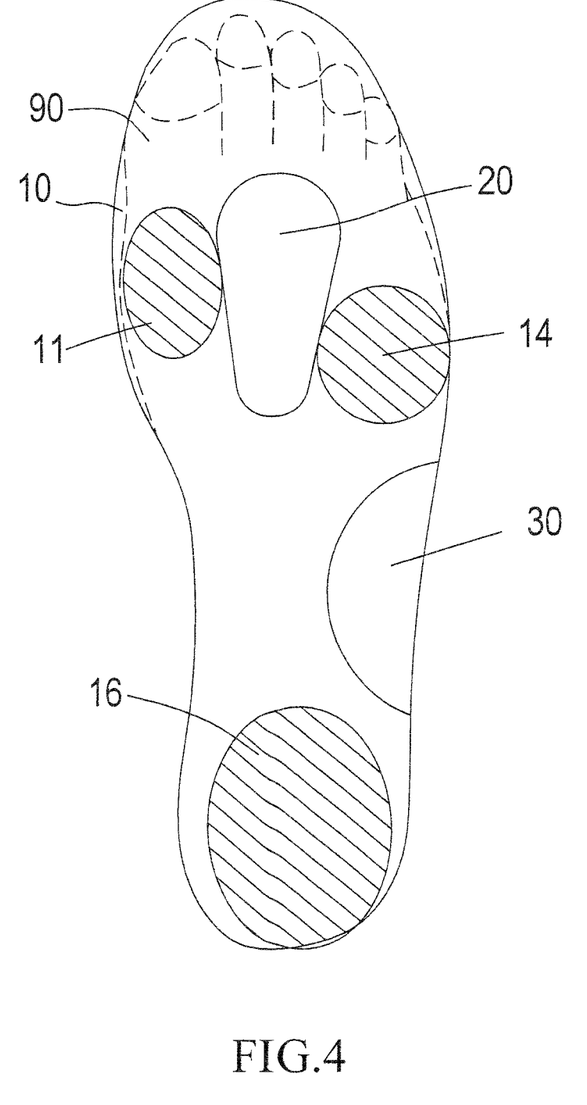
FIG. 4 is a schematic view illustrating use of the preferred embodiment of the present invention.
Figure 5:
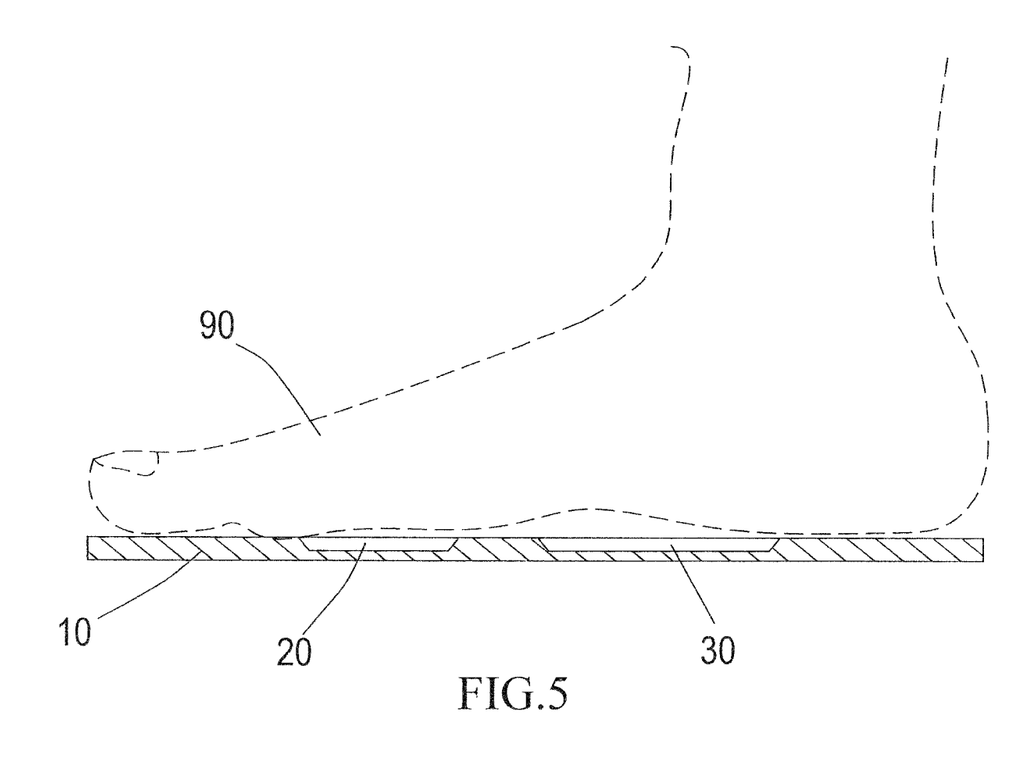
FIG. 5 is another schematic view illustrating use of the preferred embodiment of the present invention.

Referring to FIGS. 4 and 5, in use, the main body (10) is placed under the foot sole. Since in the instant embodiment, the primary adjustment structure (20) is configured as a top recessed cavity structure, the first metatarsal bone site and the fourth metatarsal bone site of the foot sole are allowed to contact the first metatarsal bone section (11) and the fourth metatarsal bone section (14) of the main body to thereby bear forces acting thereon, yet the first specific portion of the foot sole that is located between the first metatarsal bone site and the fourth metatarsal bone site does not engage the primary adjustment structure (20), so that force acting on the first specific portion can be effectively reduced. As such, the force incurring in standing or walking can be distributed to the first metatarsal bone site and the fourth metatarsal bone site of the foot sole, whereby a three-point support can be formed on the main body (10) among the first metatarsal bone section (11), the fourth metatarsal bone section (14) and the foot heel site (96). It is understood from the above description that in the configuration that the primary adjustment structure (20) is shaped as a top recessed cavity, the primary adjustment structure (20) is formed at a location lower than the top surface of the main body (10) in such a structure that achieves the purposes of the present invention.

Figure 6:
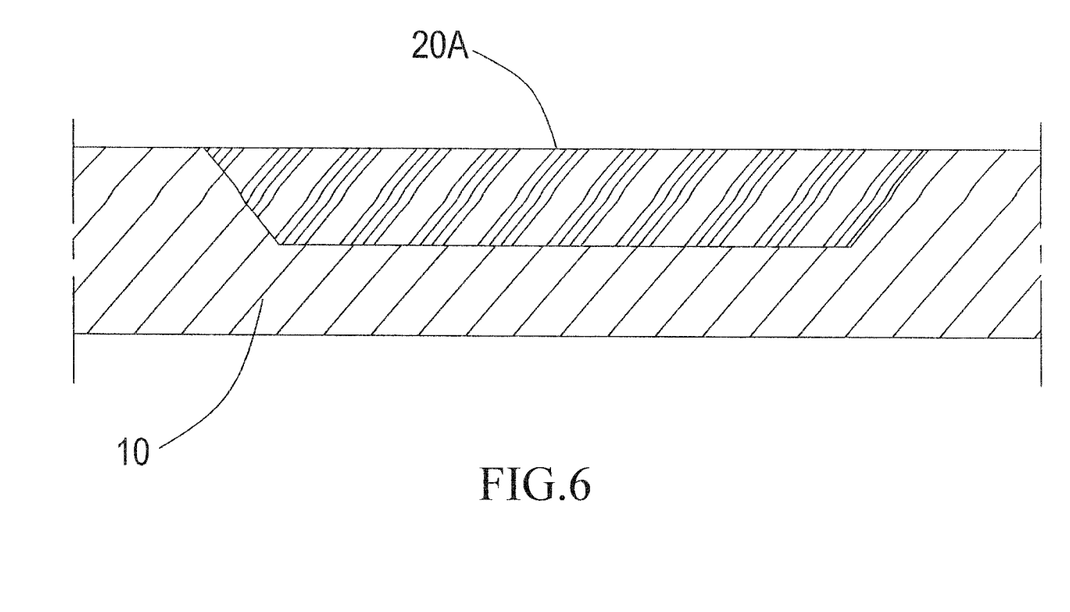
FIGS. 6-12 are cross-sectional views showing different embodiments of a primary adjustment structure according to the present invention.

Besides being formed as a top recessed cavity, as shown in FIG. 6, in a feasible configuration, the primary adjustment structure (20) is made of a soft material and the soft material is softer than the cushioning material that makes the main body. The soft material is embedded in the top surface of the main body to form a top embedding soft material structure that serves as a primary adjustment structure (20A).

Figure 7:
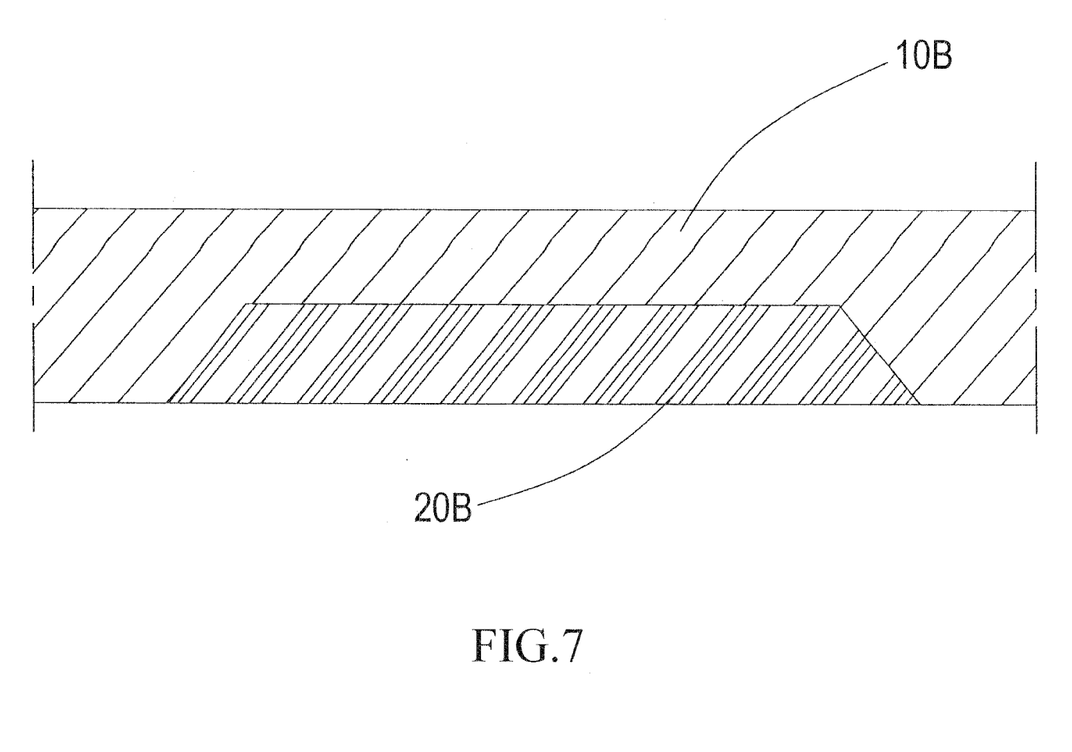
Figure 8:
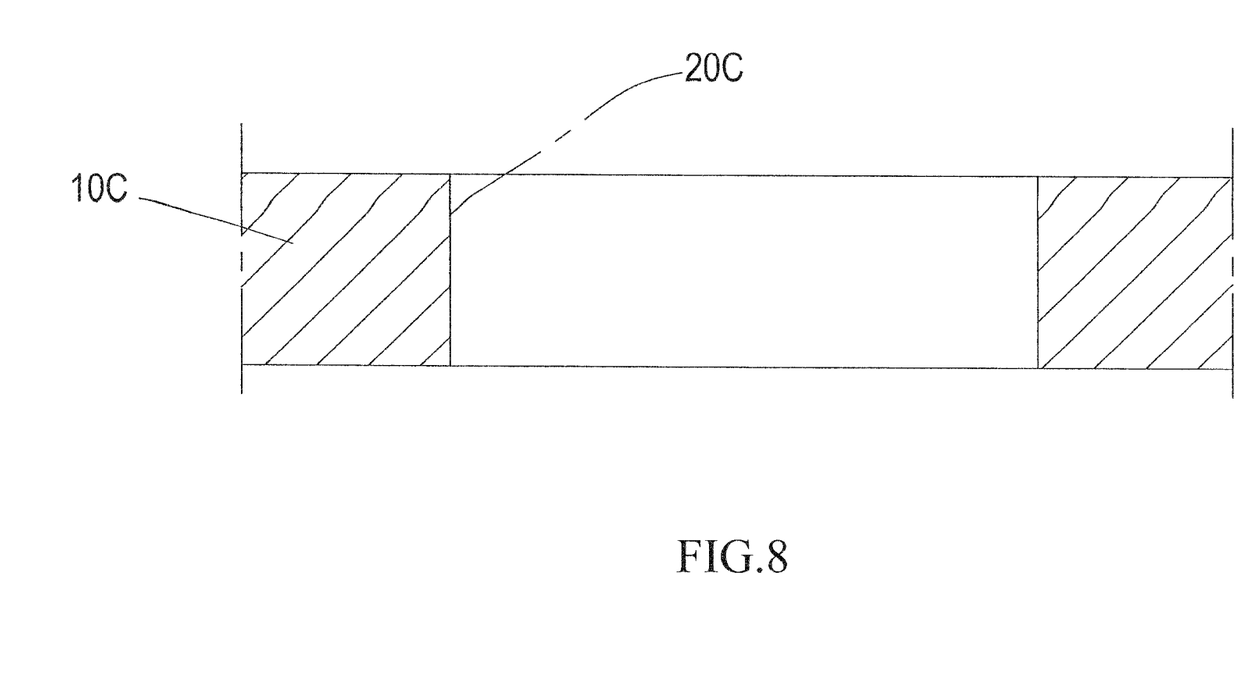
Figure 9:
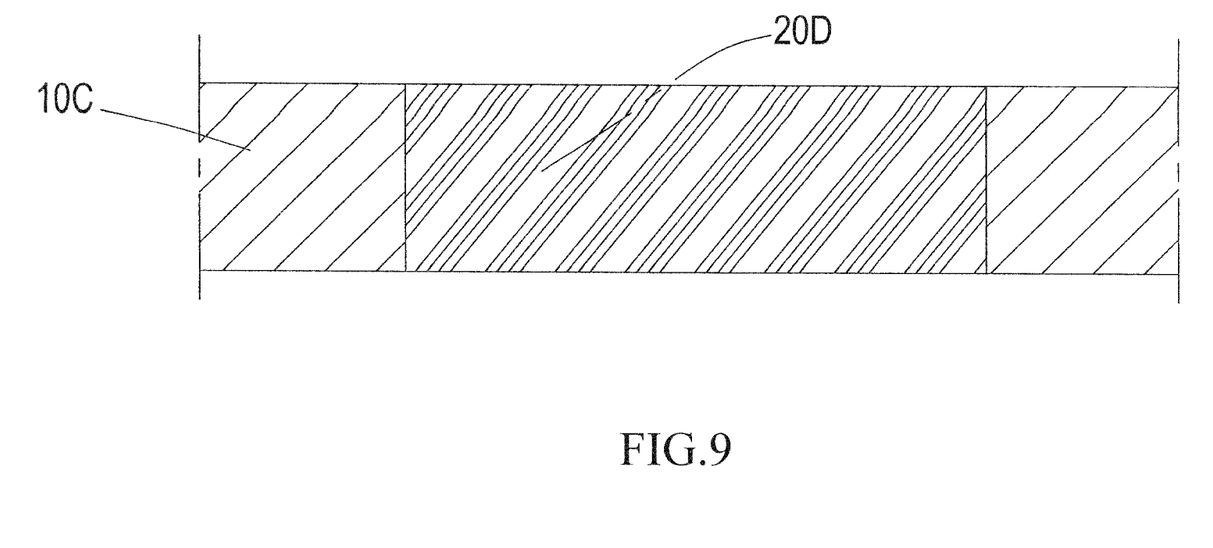
Figure 10:
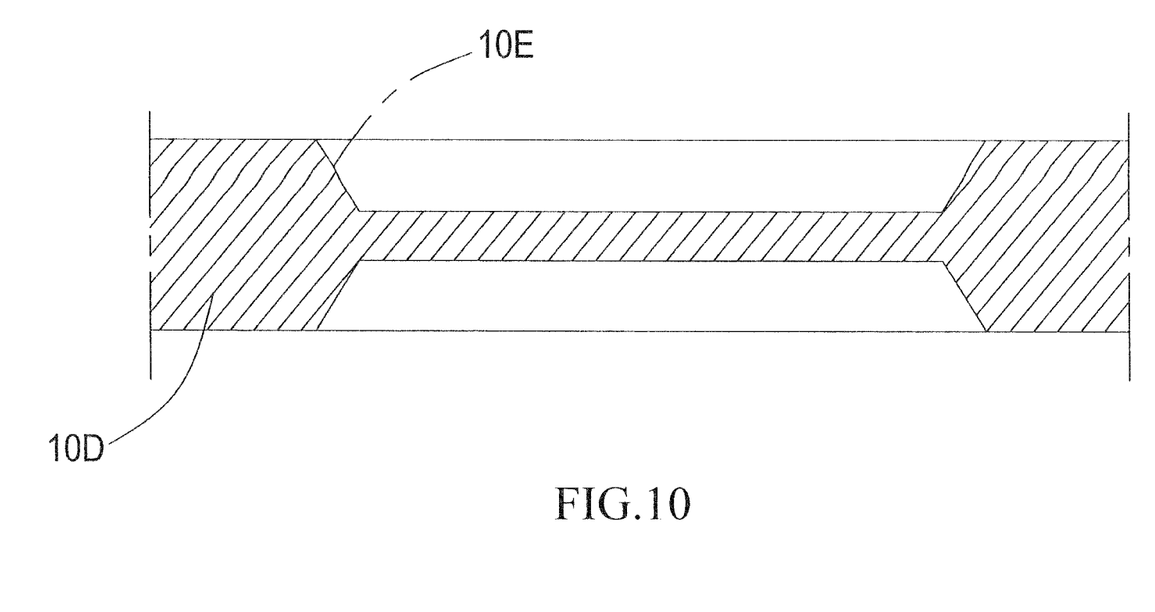
Figure 11:
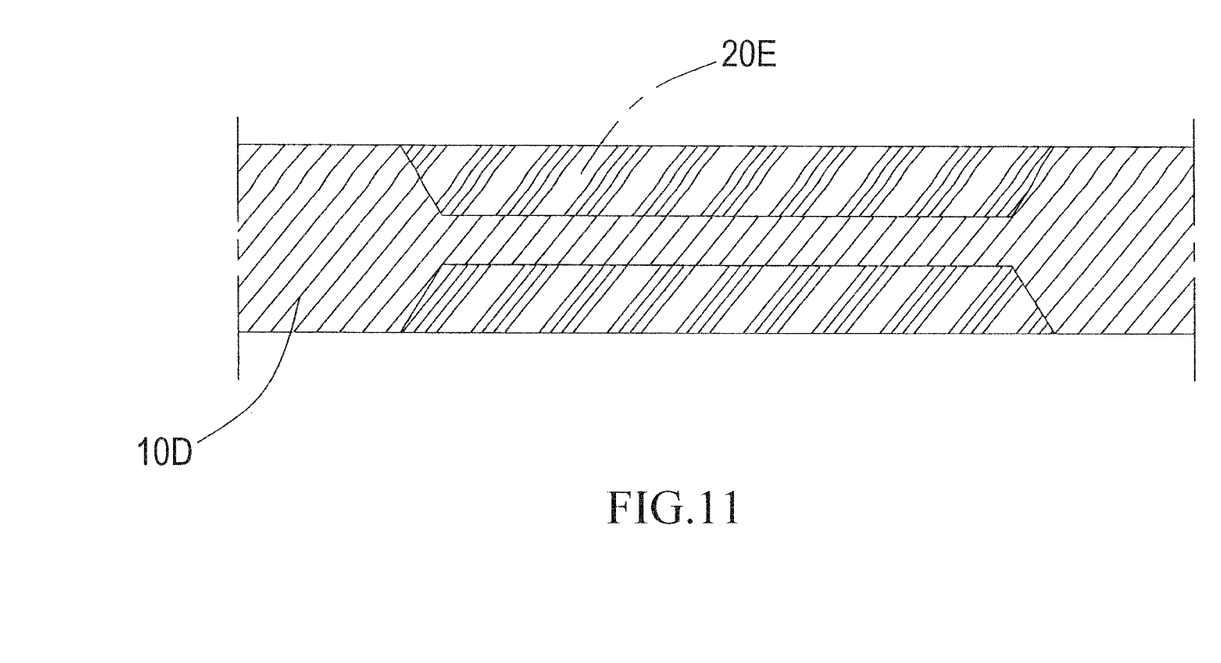
Figure 12:
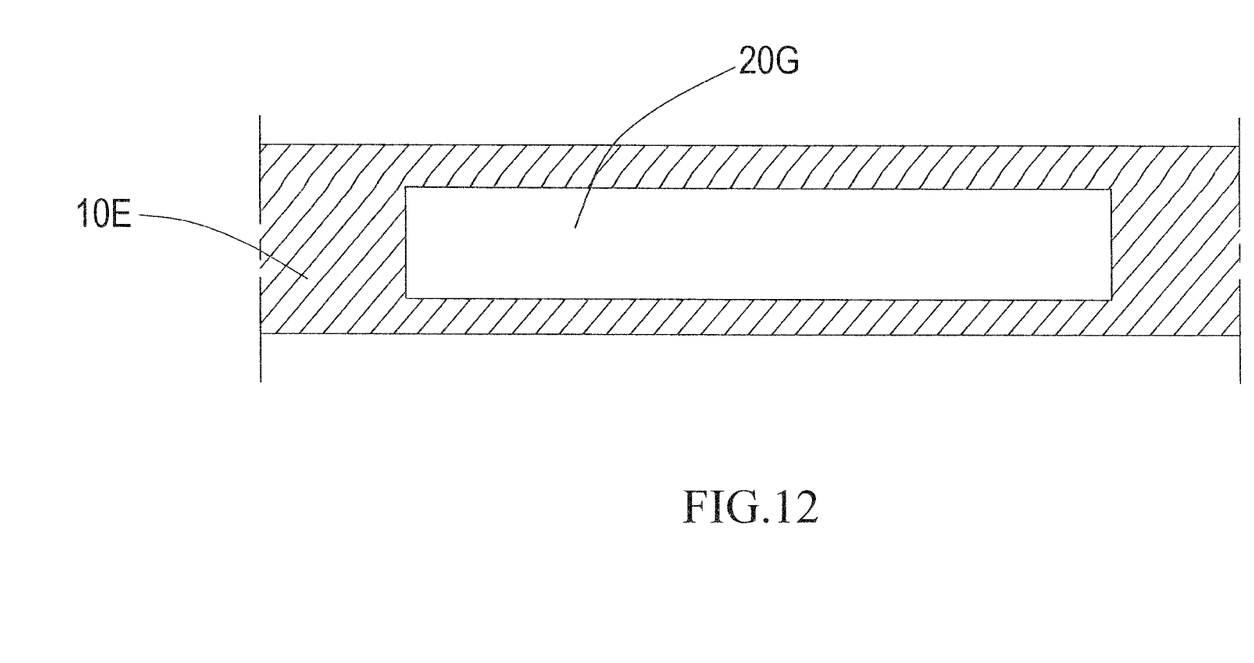

Referring to FIG. 7, in other feasible configurations, the main body (10B) forms a bottom-recessed cavity structure to serve as a primary adjustment structure, and an additional piece of soft material can be embedded therein to form a bottom embedding soft material structure to serve as the primary adjustment structure (20B). The primary adjustment structure (20B) of the previously discussed bottom-recessed cavity structure can form a flat surface which is even with the bottom surface of the main body (10B). Referring to FIG. 8, in other feasible configurations, a main body (10C) forms a through hole structure to serve as a primary adjustment structure (20C). Further, as shown in FIG. 9, a soft material is embedded to form a soft material embedded structure that serves as a primary adjustment structure (20D). Referring to FIG. 10, in other feasible configurations, a main body (10D) forms therein a reduced-thickness thin plate structure to serve as a primary adjustment structure (20E), and as shown in FIG. 11, soft materials are embedded therein to form a top and bottom embedding soft material structure that serves as a primary adjustment structure (20F). Referring to FIG. 12, in other feasible configurations, a main body (10E) forms therein an internal void to form a hollow structure that serves as a primary adjustment structure (20G), and also, soft material can be filled in the interior space of the main body (10E) to form an internally filled soft material structure that serves as the primary adjustment structure. It is understood from the above description that when soft material is used, it is arranged to have the primary adjustment structure (20A, 20B, 20D, 20F) show a hardness less than that of the main body (10, 10B, 10C,10D) so that such a structure may distribute forces to the first metatarsal bone site and the fourth metatarsal bone site of the foot sole thereby achieving the purposes of the present invention.

Similar to the previously discussed configurations of the primary adjustment structure (20), the secondary adjustment structure (30), besides being formed as a top recessed cavity structure as discussed previously, can be formed as a through hole structure or a soft material embedding structure, a bottom recessed cavity structure, a top embedding soft material structure, a bottom embedding soft material structure, a reduced-thickness thin plate structure, a top and bottom embedding soft material structure, a hollow structure or an internally-filling soft material structure, but is not limited thereto.

The above description shows the specific structure and use of the present invention, which allows of the formation of a three point support among the site to which the first metatarsal bone portion of foot sole corresponds, the site to which the fourth metatarsal bone of the foot sole corresponds, and the foot heel site, whereby the bone and muscle systems of human body can naturally maintain a neutral balanced position when standing or walking thereby assuming an ideal condition to alleviates potential damage caused by unbalance of bones and muscles and improve the troubles of sores and aches and chronic pains of human body.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A body balance device, comprising:
   a main body, which is positionable under a human foot sole and is made of a cushioning material and comprises a top surface, a bottom surface, a first metatarsal bone section corresponding to a first metatarsal bone site of the human foot sole, a fourth metatarsal bone section corresponding to a fourth metatarsal bone site of the human foot sole, and a foot heel section corresponding to human foot heel;
   a primary adjustment structure, which is disposed on the main body and is in the form of an asymmetric oval shape located between the first metatarsal bone section and the fourth metatarsal bone section and has a structure selected from a through hole structure, a top recessed cavity structure, a reduced thickness thin plate structure, and a hollow structure, wherein the asymmetric oval shape is asymmetric in a transverse axis but is symmetric in a vertical axis; and
   a secondary adjustment structure, which is located between the fourth metatarsal bone section and the foot heel section and corresponding to an outside arch of the human foot sole and has a structure selected from a through hole structure, a top recessed cavity structure, a reduced thickness thin plate structure, and a hollow structure, wherein the secondary adjustment structure has a contour having a curve side and a straight side, and the straight side superimposes on a perimeter of the main body.

2. The body balance device according to claim 1, wherein the primary adjustment structure in the form of the asymmetric oval has a tapering end that extends in a direction toward the foot heel section to reach a position corresponding to an upper edge of human foot arch.

3. The body balance device according to claim 1, wherein the primary adjustment structure and the secondary adjustment structure each comprise a top recessed cavity structure, and each of the top recessed cavity structures of the primary adjustment structure and the secondary adjustment structure further comprises a soft material filled in a top recessed cavity thereof to form a flat surface which is even with the top surface and the soft material is softer than the cushioning material of the main body.

4. The body balance device according to claim 1, wherein the main body is made in the form of a midsole.

5. The body balance device according to claim 1, wherein the main body is made in the form of a shoe pad.

6. The body balance device according to claim 2, wherein the primary adjustment structure and the secondary adjustment structure each comprise a top recessed cavity structure, and each of the top recessed cavity structures of the primary adjustment structure and the secondary adjustment structure further comprises a soft material filled in a top recessed cavity thereof to form a flat surface which is even with the top surface and the soft material is softer than the cushioning material of the main body.

7. The body balance device according to claim 2, wherein the main body is made in the form of a midsole.

8. The body balance device according to claim 2, wherein the main body is made in the form of a shoe pad.

9. The body balance device according to claim 3, wherein the main body is made in the form of a midsole.

10. The body balance device according to claim 3, wherein the main body is made in the form of a shoe pad.

11. The body balance device according to claim 1, wherein the primary adjustment structure and the secondary adjustment structure each comprise a through hole structure, and each of the through hole structures of the primary adjustment structure and the secondary adjustment structure further comprises a soft material filled in a through hole thereof and the soft material is softer than the cushioning material of the main body.

12. The body balance device according to claim 1, wherein the primary adjustment structure and the secondary adjustment structure each comprise a reduced thickness thin plate structure, and each of the reduced thickness thin plate structures of the primary adjustment structure and the secondary adjustment structure has a top recessed cavity and a bottom recessed cavity and further comprises a soft material filled in the top recessed cavity and the bottom recessed cavity and the soft material is softer than the cushioning material of the main body.

13. The body balance device according to claim 1, wherein the primary adjustment structure and the secondary adjustment structure each comprise a hollow structure, and each of the hollow structures of the primary adjustment structure and of the secondary adjustment structure has an internal void and further comprises a soft material filled in the internal void and the soft material is softer than the cushioning material of the main body.

14. A body balance device, comprising:
a main body, which is positionable under a human foot sole and is made of a cushioning material and comprises a top surface, a bottom surface, a first metatarsal bone section corresponding to a first metatarsal bone site of the human foot sole, a fourth metatarsal bone section corresponding to a fourth metatarsal bone site of the human foot sole, and a foot heel section corresponding to human foot heel;
a primary adjustment structure, which is disposed on the main body and is in the form of an asymmetric oval located between the first metatarsal bone section and the fourth metatarsal bone section, wherein the asymmetric oval shape is asymmetric in a transverse axis but is symmetric in a vertical axis; and
a secondary adjustment structure, which is located between the fourth metatarsal bone section and the foot heel section and corresponding to an outside arch of the human foot sole;
wherein each of the primary adjustment structure and the secondary adjustment structure has a bottom recessed cavity structure with a soft material filled in its bottom recessed cavity to form a flat surface which is even with the bottom surface of the main body, wherein the soft material is softer than the cushioning material of the main body, and wherein the secondary adjustment structure has a contour having a curve side and a straight side, and the straight side superimposes on a perimeter of the main body.

15. The body balance device according to claim 14, wherein the primary adjustment structure in the form of the asymmetric oval has a tapering end extends in a direction toward the foot heel section to reach a position corresponding to an upper edge of human foot arch.

16. The body balance device according to claim 14, wherein the main body is made in the form of a midsole or a shoe pad.

17. The body balance device according to claim 15, wherein the main body is made in the form of a midsole or a shoe pad.

* * * * *